US007101948B2

(12) United States Patent
Mayorga et al.

(10) Patent No.: US 7,101,948 B2
(45) Date of Patent: *Sep. 5, 2006

(54) STABILIZERS TO INHIBIT THE POLYMERIZATION OF SUBSTITUTED CYCLOTETRASILOXANE

(75) Inventors: Steven Gerard Mayorga, Oceanside, CA (US); Manchao Xiao, San Diego, CA (US); Thomas Richard Gaffney, Carlsbad, CA (US); Robert George Syvret, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 256 days.

This patent is subject to a terminal disclaimer.

(21) Appl. No.: 10/602,279

(22) Filed: Jun. 23, 2003

(65) Prior Publication Data

US 2004/0054114 A1    Mar. 18, 2004

Related U.S. Application Data

(63) Continuation-in-part of application No. 10/029,892, filed on Dec. 21, 2001, now Pat. No. 6,858,697.

(51) Int. Cl.
*C07F 7/21* (2006.01)

(52) U.S. Cl. .................. 528/31; 556/451; 556/460; 524/588

(58) Field of Classification Search ................ 528/31; 556/451, 460; 524/588
See application file for complete search history.

(56) References Cited

U.S. PATENT DOCUMENTS

| | | | |
|---|---|---|---|
| 2,837,550 A | 6/1958 | Prober | 260/448.2 |
| 3,344,111 A | 9/1967 | Chalk | 260/46.5 |
| 3,882,083 A | 5/1975 | Berger et al. | 260/46.5 |
| 3,998,865 A | 12/1976 | Siciliano et al. | 260/448.2 |
| 5,028,566 A | 7/1991 | Lagendijk | 437/238 |
| 5,118,735 A * | 6/1992 | Burnier | 524/99 |
| 5,380,812 A | 1/1995 | Lutz et al. | 528/15 |
| 5,548,006 A | 8/1996 | Hirabayashi et al. | 524/82 |
| 6,368,359 B1 | 4/2002 | Perry et al. | 8/142 |
| 2003/0149213 A1 | 8/2003 | Mayorga et al. | |
| 2004/0039219 A1 | 2/2004 | Chen et al. | |
| 2004/0127070 A1 | 7/2004 | Teff et al. | |

FOREIGN PATENT DOCUMENTS

JP    7145179    8/1999

WO    WO 02/43119    5/2002

OTHER PUBLICATIONS

"User's Guide For: Glass Deposition With Teos," Dr. Arthur K. Hochberg, Schumacher, 1992.
Extrema® TOMCATS®, (Tetramethylcyclotetrasiloxane) Schumacher, 2000.
"Modeling of Low-Pressure Deposition of $SiO_2$ by Decomposition . . . ," Huppertz, et al, Schumacher, 1979.
"The Deposition of Silicon Dioxide Films at Reduced Pressure," Adams, et al, J. Electrochem Soc. 1979.
"Preparation of Device-quality $SiO_2$ Thin Films by Remote..," G. Lucovsky, Adv. Mat. Optics. . , 1996.
"Deposition of Silicon Oxide Films From TEOS By Low..," G. Tochitani, et al, J. Vac. Sci. Tech. A, 1993.
"Properties of Silicon Dioxide Films Deposited at Low..," S.K. Ray, et al, J. Vac. Sci. Tech. B, 1992.
"Electron Cyclotron Resonance Microwave Discharge for Oxide..," J. Electrochem Soc. 1992.
"Ion and Chemical Radical Effects on the Step Coverage..," C.-P. Chang, et al, J. Appl. Phys. 67, 1990.
"Electron Cyclotron Resonance Microwave Discharge for Oxide..," C.S. Pai, et al, J. Appl. Phys. 1993.
"User's Guide For: Undoped Glass, PSG, and BPSG Using..," Schumacher, 1991.
"An Overview of the Polymerization of Cyclosiloxanes..," J.E. McGrath, et al, ACS Symp., 1983.
English language translation JP 07-145179.
JP 07 145179 A: Patent Abstracts of Japan, vol. 1995, No. 09, Oct. 31, 1995.
XP-002233220: Derwent Publications Ltd., London, GB; AN 1980-10616C.
XP-002233221: Derwent Publications Ltd., London, GB, AN 1997-72075Y.

* cited by examiner

*Primary Examiner*—Margaret G. Moore
(74) *Attorney, Agent, or Firm*—Geoffrey L. Chase; Rosaleen P. Morris-Oskanian; Joseph D. Rossi

(57) ABSTRACT

The present invention is; (a) a process for stabilizing a cyclotetrasiloxane, such as 1,3,5,7-tetramethylcyclotetrasiloxane, against polymerization used in a chemical vapor deposition process for silicon oxides in electronic material fabrication comprising providing an effective amount of a free radical scavenger polymerization inhibitor to such cyclotetrasiloxane; and (b) a composition of a cyclotetrasiloxane, such as 1,3,5,7-tetramethylcyclotetrasiloxane, stabilized against polymerization used in a chemical vapor deposition process as a precursor for silicon oxides in electronic material fabrication, comprising; such cyclotetrasiloxane and a free radical scavenger polymerization inhibitor.

10 Claims, No Drawings

STABILIZERS TO INHIBIT THE POLYMERIZATION OF SUBSTITUTED CYCLOTETRASILOXANE

CROSS-REFERENCE TO RELATED APPLICATIONS

This application is a continuation-in-part of U.S. application Ser. No. 10/029,892, now U.S. Pat. No. 6,858,697, filed Dec. 21, 2001, which is incorporated herein by reference in its entirety.

BACKGROUND OF THE INVENTION

Silicon dioxide films have been used for some time in the fabrication of integrated circuits (IC) for semiconductor device manufacturing. There are many examples of the preparation of such thin films of $SiO_2$ in the open and patent literature. See, for example, the publications of the Schumacher Group, Air Products and Chemicals, Inc., e.g. User's Guide For: Glass Deposition with TEOS[1], and Extrema® TEOS (Tetraethyl Orthosilicate) Product Data Sheet[2]. See also, Modeling of Low-Pressure Deposition of $SiO_2$ by Decomposition of TEOS[3], and The Deposition of Silicon Dioxide Films at Reduced Pressure[4]. There are numerous journal articles that review various CVD techniques for the deposition of $SiO_2$ and the properties of thin films deposited using such techniques[5-9].

Early $SiO_2$ films were deposited by CVD oxidation of silane ($SiH_4$). New source materials were needed in order to maintain good step coverage as sub-micron patterned electronic devices were developed. Films deposited from tetraethylorthosilcate (TEOS) show superior step coverage properties compared to $SiH_4$[7]. TEOS is considered an industry standard source for the CVD preparation of $SiO_2$. TEOS is a volatile liquid, providing for efficient vapor delivery and general ease of handling. It is nonpyrophoric, and therefore, provides a significant safety advantage over silane. It produces dielectric films with excellent electrical and mechanical properties suitable for many device manufacturing applications.

The chemical 1,3,5,7-Tetramethylcyclotetrasiloxane (such as TOMCATS® siloxane available from Schumacher of Carlsbad, Calif.) is under development as a new source material for the CVD preparation of $SiO_2$ glass[10-11]. TOMCATS type siloxane is a high purity volatile liquid precursor chemical that is specifically designed to satisfy the critical demands of the semiconductor device manufacturing industry. Like TEOS, TOMCATS type siloxane can be used for the chemical vapor deposition of glasses and doped glasses for various dielectric film applications such as trench fill, interlevel dielectric, gate and thick oxide[2]. It provides similar safety advantages because of its non-pyrophoric and noncorrosive nature. The normal boiling points of TOMCATS type siloxane and TEOS are 135° C. and 168° C., respectively. The higher volatility of TOMCATS type siloxane allows it to be delivered at lower temperature or with higher efficiency at comparable temperature. Its deposition rate is 10 times that of TEOS at 600° C., with a deposition efficiency 3 times that of TEOS[2]. It is superior to silane and similar to TEOS in the conformality and step coverage of the resulting films[11-12].

In general, $SiO_2$ films deposited from TOMCATS type siloxane exhibit excellent mechanical and electrical properties. The films are dense with low carbon content and refractive index values comparable to thermal oxide. TOMCATS type siloxane is effective for low-pressure chemical vapor deposition (LPCVD) and as a liquid injection source for plasma enhanced chemical vapor deposition (PECVD). The later method utilizes plasmas rather than thermal energy to promote chemical reactions. TOMCATS type siloxane PECVD is typically run at lower temperature than LPCVD (400° C. vs. 500–600° C.).

Despite these advantages, TOMCATS type siloxane has experienced limited acceptance as a CVD source for the manufacturing of semiconductor devices. One disadvantage of TOMCATS type siloxane is its instability with respect to polymerization[13] when exposed to certain chemicals or process conditions. This results in a lower volatility liquid or gel that creates CVD process handling issues. TOMCATS type siloxane polymerization is catalyzed by acid, base or free radicals.

Prolonged heating of TOMCATS type siloxane (Example 1) has also been shown experimentally in the present invention to promote polymerization. The degree of polymerization can be very minor, accounting for only several tenths of a percent. Under more severe conditions of prolonged exposure to elevated temperature or to certain acids or bases, substantial polymerization will occur, resulting in a highly viscous liquid or gel containing over 10% by weight of oligomeric or polymeric material.

Several references in the prior art relate to the stabilization of siloxane. Hirabayashi et al.[14] teach the use of a triazine or sulfide "control agent" to stabilize a mixture comprising an aliphatic unsaturated group, containing an organopolysiloxane compound, such as TOMCATS type siloxane, and a platinum group catalyst. Those inventors teach the use of the triazine or sulfide agent to give a mixture that is stable and resistant to premature gelation at room temperature and thus providing extended storage stability.

Lutz et al.[15] disclose the use of di- and trihydrocarbylphosphines which act as curing inhibitors for compositions comprising: (1) alkenyl radicals; (2) compounds containing silicon-bonded hydrogen atoms (e.g., TOMCATS type siloxane); and (3) a platinum group metal catalyst. Lutz et al. claim that the inhibitor functions by complexing with the platinum catalyst rendering it inactive for subsequent curing.

In a similar patent, Chalk[16] teaches the use of acrylonitrile type compounds that reduce the activity of the platinum catalyst deterring the copolymerization of various mixtures of polysiloxanes.

Berger et al.[17] propose the use of an ethylenically unsaturated isocyanurate which functions in a like manner to deactivate the Pt catalyst rendering a curable organopolysiloxane composition stable to premature gelation.

Endo et al.[18] teach the stabilization of cyclosiloxanes, such as TOMCATS type siloxane through the use of 1 to 20 weight % of polymethylpolysiloxanes, such as 1,1,1,3,5,5,5-heptamethyltrisiloxane.

The patent references cited all teach the use of various agents that in one manner or another inhibit the polymerization or co-polymerization of polysiloxanes for various applications in the silicon rubber industry. None of them specify or suggest applications as polymerization inhibitors for CVD sources in the semiconductor device manufacturing industry.

BRIEF SUMMARY OF THE INVENTION

The present invention is a process for stabilizing a substituted cyclotetrasiloxane against polymerization used in a chemical vapor deposition process for silicon oxides in electronic material fabrication comprising providing an effective amount of a free radical scavenger polymerization inhibitor to a substituted cyclotetrasiloxane having the following formula:

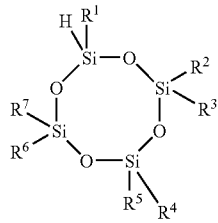

where $R^{1-7}$ are individually selected from the group consisting of hydrogen, a normal, branched or cyclic $C_{1-10}$ alkyl group, and a $C_{1-4}$ alkoxy group.

The present invention is also a composition of substituted cyclotetrasiloxane stabilized against polymerization used in a chemical vapor deposition process as a precursor for silicon oxides in electronic material fabrication, comprising; (a) a substituted cyclotetrasiloxane having the following formula:

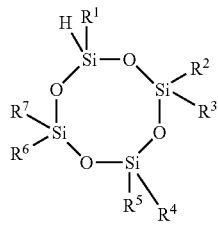

where $R^{1-7}$ are individually selected from the group consisting of hydrogen, a normal, branched or cyclic $C_{1-10}$ alkyl group, and a $C_{1-4}$ alkoxy group, and (b) a free radical scavenger.

DETAILED DESCRIPTION OF THE INVENTION

The chemical 1,3,5,7-tetramethylcyclotetrasiloxane (such as TOMCATS® siloxane available from Schumacher of Carlsbad, Calif.) is used as a precursor for the chemical vapor deposition (CVD) of $SiO_2$ for semiconductor device manufacturing. TOMCATS type siloxane is currently under evaluation by semiconductor device manufacturers for use as a CVD precursor for $SiO_2$ because of its ability to form high quality films with excellent electronic and mechanical properties. TOMCATS type siloxane is known to polymerize when subjected to extended periods of heating or upon exposure to certain chemicals. In this invention we disclose the use of various free radical scavengers that inhibit the polymerization of TOMCATS type siloxane. The low concentration of the additive does not significantly impact the overall product purity, nor is it anticipated to have a negative impact on the critical properties of the resulting films produced by CVD.

Therefore, an object of the present invention is to eliminate or inhibit the polymerization of TOMCATS type siloxane under typical CVD process conditions. These TOM CATS type siloxanes include substituted cyclotetrasiloxanes of the formula:

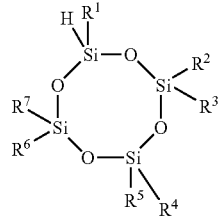

where $R^{1-7}$ are individually selected from the group consisting of hydrogen, a normal, branched or cyclic $C_{1-10}$ alkyl group, and a $C_{1-4}$ alkoxy group.

This is done through the use of additives that inhibit the polymerization of TOMCATS type siloxane under conditions that would normally favor polymerization. The present invention demonstrates that certain additives are effective at inhibiting polymerization, such as free radical scavengers. TOMCATS type siloxanes are sensitive to oxygen, carbon dioxide and nitrogen trifluoride ($NF_3$) at elevated temperatures. TOMCATS type siloxanes react with oxygen forming oligomeric and polymeric species at temperatures equal to or greater than 60° C. This is significant because oxygen, carbon dioxide and nitrogen trifluoride are commonly used in the manufacture of semiconductor devices, such as the oxidizing gas in plasma enhanced chemical vapor deposition (PECVD) processes for the deposition of $SiO_2$ films from TOMCATS type siloxane. These scavengers work by deterring chemical reactions that proceed by a free-radical reaction pathway. The free radical scavengers contemplated as $O_2$-, $CO_2$- and/or $NF_3$-stabilizers are 2,6-di-tert-butyl-4-methyl phenol (or BHT for butylhydroxytoluene), 2,2,6,6-tetramethyl-1-piperidinyloxy (TEMPO), 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl) propionate, tetrakis (methylene (3,5-di-tert-butyl) -4-hydroxy-hydrocinnamate) methane, phenothiazines, alkylamidonoisoureas, thiodiethylene bis (3,5,-di-tert-butyl-4-hydroxy-hydrocinnamate, 1,2,-bis (3,5-di-tert-butyl-4-hydroxyhydrocinnamoyl) hydrazine, tris (2-methyl-4-hydroxy-5-tert-butylphenyl) butane, cyclic neopentanetetrayl bis (octadecyl phosphite), 4,4'-thiobis (6-tert-butyl-m-cresol), 2,2'-methylenebis (6-tert-butyl-p-cresol), oxalyl bis (benzylidenehydrazide) and naturally occurring antioxidants such as raw seed oils, wheat germ oil, tocopherols and gums.

Preferably, the free radical scavenger is provided in an amount of 10–1000 ppm (wt.); more preferably an amount of of 50–500 ppm (wt.); most preferably, an amount of 50–250 ppm (wt.); optimally, an amount of of 100–200 ppm (wt.).

To attain the object of the present invention, to eliminate or inhibit the polymerization of TOMCATS type siloxane under typical CVD process conditions, a standard laboratory test was established with the intent of accelerating the normal polymerization process. The accelerated aging test is meant to simulate the normal course of gradual polymerization that would typically occur over a more protracted period of time. This test, which consists of exposing a sealed quartz ampoule of TOMCATS type siloxane to elevated temperature for 24 hours, is referred to in the present document as the "accelerated aging test". These conditions are understood to be considerably more severe than TOMCATS type siloxane would be subjected to in a typical CVD process. In a typical accelerated aging test, the ampoule is loaded with approximately 5.0 ml of TOMCATS type siloxane and, except for "control experiments", a free radical scavenger to inhibit polymerization. The TOMCATS type siloxane/additive mixture is cooled in a liquid nitrogen bath. Then, the atmosphere above the TOMCATS type siloxane is evacuated for 5 minutes. The neck of the quartz ampoule is subsequently sealed using a hydrogen/oxygen torch. The sealed ampoule is placed in an oven and held at 120° C. for 5 days. The ampoule is removed and allowed to cool to room temperature. Its contents are analyzed by gas chromatograph (GC) to measure the degree of polymerization.

The degree of polymerization is measured quantitatively by GC. This technique is very sensitive to detecting the onset of polymerization as evidenced by the formation of higher molecular weight species with longer retention times than the parent TOMCATS type siloxane peak. TOMCATS type siloxane samples that are determined to be of "high viscosity" by visual inspection are not routinely run on the GC. The oligomeric or polymeric siloxanes tend to irreversibly contaminate the stationary phase of the GC column due to their low solubility and low volatility. Such samples are qualitatively described in the present invention to have greater than 10 wt. % polymer, consistent with previous observations.

The polymerization of cyclical polysiloxanes has been determined to be catalyzed by free radicals. Laboratory observations suggest that the polymerization of TOMCATS type siloxane is particularly sensitive to exposure to oxygen or nitrogen trifluoride, both of which the siloxane is exposed to in use in semiconductor manufacture. The additives described in this invention form solutions with TOMCATS type siloxane at the tested concentrations. In addition, these additives are not anticipated to have a detrimental impact on the overall CVD process by virtue of their concentration and their chemical and physical characteristics.

In-house experiments have established that TOMCATS type siloxane is sensitive to oxygen and/or nitrogen trifluoride at elevated temperatures. TOMCATS type siloxane reacts with oxygen and/or nitrogen trifluoride forming oligomeric and polymeric species at temperatures equal to or greater than 60° C. This is particularly important since oxygen and/or nitrogen trifluoride is commonly used as the oxidizing gas in PECVD processes for the deposition of $SiO_2$ films from TOMCATS type siloxane or as a cleaning gas between production runs. Data collected for the stability of TOMCATS type siloxanes in the presence of oxygen, carbon dioxide and nitrogen trifluoride are shown in Table1.

To address this reactivity TOMCATS type siloxane was spiked with low levels of chemicals which function as free radical scavengers, i.e., antioxidants. These scavengers work by deterring chemical reactions that proceed by a free-radical reaction pathway. The free radical scavenger investigated as $O_2$-, $CO_2$- and/or nitrogen trifluoride- stabilizers was 2,6-di-tert-butyl-4-methyl phenol (or BHT for butylhydroxytoluene. TOMCATS type siloxane was substantially more resistant toward $O_2$, $CO_2$ and/or nitrogen trifluoride when spiked with BHT. The addition of 150 ppm by weight of BHT greatly reduced the sensitivity of TOMCATS type siloxane toward $O_2$, $CO_2$ and/or nitrogen trifluoride at elevated temperature as shown by the series of tests run at 90° C. (Table 1). Another benefit is that BHT is free of atomic nitrogen which reportedly gives rise to undesirable basic film properties. TEMPO is also expected to be an effective $O_2$, $CO_2$ and/or nitrogen trifluoride-stabilizer.

These tests clearly established the benefit of the use of low levels of free radical scavengers to greatly reduce or eliminate the sensitivity of TOMCATS type siloxane to $O_2$, $CO_2$ and/or nitrogen trifluoride, thereby, reducing the likelihood of plugging problems occurring by the $O_2$, $CO_2$ and/or nitrogen trifluoride promoted polymerization of TOMCATS type siloxane. The scavengers/antioxidants contemplated for this utility include: 2,6-di-tert-butyl-4-methyl phenol, 2,2,6,6-tetramethyl-1-piperidinyloxy, 2-tert-butyl-4-hydroxyanisole, 3-tert-butyl-4-hydroxyanisole, propyl ester 3,4,5-trihydroxy-benzoic acid, 2-(1,1-dimethylethyl) -1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert -butyl-4-hydroxyphenyl) propionate, tetrakis (methylene (3,5-di-tert-butyl)-4-hydroxy-hydrocinnamate) methane, phenothiazines, alkylamidonoisoureas, thiodiethylene bis (3,5,-di-tert-butyl-4-hydroxy-hydrocinnamate, 1,2,-bis (3,5-di-tert -butyl-4-hydroxyhydrocinnamoyl) hydrazine, tris (2-methyl-4-hydroxy-5-tert-butylphenyl) butane, cyclic neopentanetetrayl bis (octadecyl phosphite), 4,4'-thiobis (6-tert-butyl-m-cresol), 2,2'-methylenebis (6-tert-butyl-p-cresol), oxalyl bis (benzylidenehydrazide) and mixtures thereof. Naturally occurring antioxidants can also be used such as raw seed oils, wheat germ oils tocopherols and gums.

The polymerization of TOMCATS type siloxanes is known to be catalyzed by free radicals. The present invention demonstrates that certain free radical scavengers are effective additives for inhibiting the polymerization of TOMCATS type siloxanes, such as 2,6-di-tert-butyl-4-methyl phenol, also known as butylhydroxytoluene (BHT).

To attain the object of the present invention, to eliminate or inhibit the polymerization of TOMCATS type siloxane under typical CVD process conditions, laboratory experiments were run with the intent of simulating conditions that TOMCATS type siloxane would be subject to in a typical CVD process. The effectiveness of these inhibitors was gauged by comparing the stability of neat TOMCATS type siloxane (i.e., no polymerization inhibitor) with that of TOMCATS type siloxane stabilized with free radical scavengers such as BHT. These stability tests were carried out at 90° C. in the absence of contaminants (under vacuum), and in presence of contaminants, in which TOMCATS type siloxane was intentionally exposed to controlled amounts of selected gases such as $O_2$, $CO_2$ and nitrogen trifluoride. All three of these gases are typically used at some point in the processing or maintenance for the chemical vapor deposition of $SiO_2$ from TOMCATS type siloxane precursor. Oxygen and $NF_3$ are known sources of free radicals. TOMCATS type siloxane is often diluted with $O_2$ and/or $CO_2$ during a typical PECVD process. Nitrogen trifluoride is commonly used in the chamber-cleaning step of such processes.

EXAMPLE 1

Polymerization Under Vacuum Conditions

Stability of TOMCATS Type Siloxane, With and Without BHT

Six quartz ampoules with a nominal volume of 80–90 ml were used for this test. These ampoules will be referred to in the present example as 1A, 1B, 1C, 1D, 1E and 1F. These ampoules were prepared by rinsing twice with distilled water, twice with reagent grade acetone, then placed into a drying oven at 175° C. for 16–18 hours. The dry ampoules were removed from the oven and used while still warm. Approximately 5.0 ml of additive free TOMCATS type siloxane was loaded into ampoules 1A, 1B, 1C and 1D. A similar amount of TOMCATS type siloxane containing 150 ppm (by weight) BHT was loaded into ampoules 1E and 1F. Teflon valves were attached to the open end of the ampoules. The end of ampoule 1A was immersed in a liquid nitrogen bath to cause any vaporized TOMCATS type siloxane to condense. The air was evacuated from the headspace of the ampoule by subjecting it to vacuum for 5 minutes. The ampoule was sealed at the neck using a hydrogen/oxygen torch. The remaining 5 ampoules (1B–1F) were sealed in a similar fashion. Sealed ampoules 1C, 1D, 1E and 1F were placed in a nitrogen-purged oven, and subsequently held at a constant temperature of 90° C. for 24 hours. Ampoules 1A and 1B were kept at room temperature and served as control samples. After 24 hours the heated ampoules were removed from the oven and allowed to cool to room temperature.

GC analysis showed no significant polymerization for the control samples (1A, 1B) relative to the lot material. The heated samples with no additive (1C, 1D) showed an average polymerization of 0.136%. The heated samples with 150 ppm BHT had an average polymerization of 0.079%. Results are summarized in Table 1.

EXAMPLE 2

Sensitivity to Carbon Dioxide

Exposure of TOMCATS Type Siloxane to 0.50 Weight % Carbon Dioxide

Four quartz ampoules (2A, 2B, 2C and 2D) were cleaned and dried as described in Example 1. Approximately 5.0 g of TOMCATS type siloxane containing no additive was loaded into ampoules 2A and 2B. A similar amount of TOMCATS type siloxane spiked with 150 ppm by weight of BHT was loaded into ampoules 2C and 2D. Each of the 4 Ampoules was equipped with a quartz side-arm extension, capped with a septum. Ampoule 2A was cooled to liquid nitrogen temperature and evacuated to remove the air in the headspace. The ampoule was isolated from the vacuum and 19 sccm of gaseous carbon dioxide was injected via a syringe through the septum cap on the side arm. The ampoule, still under sub-ambient pressure, was sealed using a torch as described in Example 1. The remaining 3 ampoules (2B, 2C and 2D) were prepared and sealed in the same manner. All four sealed ampoules were heated for 24 hours at 90° C. as described in Example 1. TOMCATS type siloxane without additive showed an average polymerization of 0.216%. The same chemical with 150 ppm of BHT additive showed an average polymerization of 0.028%. Results are summarized in Table 1.

EXAMPLE 3

Sensitivity to Oxygen

Exposure of TOMCATS Type Siloxane to 0.50 Weight % Oxygen

Four quartz ampoules (3A, 3B, 3C and 3D) were cleaned and dried as described in Example 1. Approximately 5.0 g of TOMCATS type siloxane containing no additive was loaded into ampoules 3A and 3B. A similar amount of TOMCATS type siloxane spiked with 150 ppm by weight of BHT was loaded into ampoules 3C and 3D. Each of the 4 ampoules was equipped with a quartz side-arm extension, capped with a septum. Ampoule 3A was cooled to liquid nitrogen temperature and evacuated to remove the air in the headspace. The ampoule was isolated from the vacuum and 19 sccm of oxygen was injected via a syringe through the septum cap on the side arm. The ampoule, still under sub-ambient pressure, was sealed using a torch as described in Example 1. The remaining 3 ampoules (3B, 3C and 3D) were prepared and sealed in the same manner. All four sealed ampoules were heated for 24 hours at 90° C. as described in Example 1. TOMCATS type siloxane without additive showed an average polymerization of 6.462%. The same chemical with 150 ppm of BHT additive showed an average polymerization of 0.031%. Results are summarized in Table 1.

EXAMPLE 4

Sensitivity to Nitrogen Trifluoride

Exposure of TOMCATS Type Siloxane Without BHT to Nitrogen Trifluoride

Compatibility tests were carried to evaluate the effectiveness of free radical scavengers, such as BHT, to inhibit the nitrogen trifluoride promoted polymerization of TOMCATS type siloxane. Because of the potential reactivity of $NF_3$ And the corrosive nature of possibly byproducts, these compatibility tests were carried out in a 300 cc stainless steel Parr Reactor.

49.956 g of TOMCATS type siloxane was loaded into the 300 cc reactor. This sample of TOMCATS type siloxane did not have BHT, but did have 125 ppm by weight 2,4-pentanedione. The 2,4-pentanedione was developed as an earlier additive to stabilize TOMCATS type siloxane. The gas in the reactor headspace was evacuated. $NF_3$ was expanded into the headspace such that its final concentration was 636 ppm by weight (0.0636 weight %). The reactor temperature was raised to 100° C. and held for 24 hours. After the specified time, the $NF_3$ was removed by pumping out the reactor. The reactor was opened. The TOMCATS type siloxane had completely gelled. There was no residual liquid in the reactor.

Samples that are very viscous or gelled, such as the one described in the present example, are indicative of a high degree of polymerization for TOMCATS type siloxane. These samples are not amenable to analysis by GC due to their insolubility in common organic solvents. Such samples are assigned a degree of polymerization of ">10 weight %" for the purpose of this document.

EXAMPLE 5

Sensitivity to Nitrogen Trifluoride

Exposure of TOMCATS Type Siloxane With 150 ppm BHT to Nitrogen Trifluoride 49.863 g of TOMCATS type siloxane was loaded into the 300 cc reactor. This sample of TOMCATS type siloxane had been previously spiked with 150 ppm by weight of BHT. The gas in the reactor headspace was evacuated. $NF_3$ was expanded into the headspace such that its final concentration was 631 ppm by weight (0.0631 weight %). The reactor temperature was raised to 100° C. and held for 24 hours. After the specified time, the $NF_3$ was removed by pumping out the reactor. The reactor was opened and 45.631 g of clear colorless liquid was recovered. The loss in weight was probably due to pumping on the reactor at the end of the experiment to remove the $NF_3$. The liquid was transferred to a polyethylene bottle. A sample was analyzed by GC, establishing that the purity of TOMCATS type siloxane stayed the same at 99.95% before and after analysis. No polymerization was detected.

TABLE 1

The stability of TOMCATS type siloxane with and without BHT inhibitor in the presence of various chemical sources of free radicals.

| Example No. | Gas in Headspace* | % Purity of TOMCATS type siloxanes (before testing) | Spiked with 150 ppm BHT? | Time @ 90° C. (hrs) | Extent of Polymerization after testing (%) | Average % Polymerization of duplicate samples (after testing) |
|---|---|---|---|---|---|---|
| 1A | None | 99.962 | No | 0 | <0.005 | <0.005 |
| 1B | None | 99.962 | No | 0 | <0.005 | |
| 1C | None | 99.962 | No | 24 | 0.113 | 0.136 |
| 1D | None | 99.962 | No | 24 | 0.159 | |
| 1E | None | 99.962 | Yes | 24 | 0.084 | 0.079 |
| 1F | None | 99.962 | Yes | 24 | 0.075 | |
| 2A | $CO_2$ | 99.962 | No | 24 | 0.242 | 0.216 |
| 2B | $CO_2$ | 99.962 | No | 24 | 0.190 | |
| 2C | $CO_2$ | 99.962 | Yes | 24 | 0.028 | 0.028 |
| 2D | $CO_2$ | 99.962 | Yes | 24 | 0.027 | |
| 3A | $O_2$ | 99.962 | No | 24 | 6.482 | 6.462 |
| 3B | $O_2$ | 99.962 | No | 24 | 6.442 | |
| 3C | $O_2$ | 99.962 | Yes | 24 | 0.006 | 0.031 |
| 3D | $O_2$ | 99.962 | Yes | 24 | 0.057 | |
| 4 | $NF_3$ | 99.93 | No | 24 ¥ | >10.0 ‡ | >10.0 |
| 5 | $NF_3$ | 99.95 | Yes | 24 ¥ | <0.01 | <0.01 |

*All contaminant gases were spiked at 0.50 weight percent, with the exception of $NF_3$ in Examples #4, and #5, that was present at 0.0636 wt. % and 0.0631 wt. %, respectively.
¥ Testing temperature was 100° C.
‡ No GC was run since this sample had fully gelled. This is indicative of >10% polymerization.

The present invention has been set forth with regard to several preferred embodiments, but the full scope of the present invention should be ascertained from the claims which follow.

The invention claimed is:

1. A process for stabilizing a cyclotetrasiloxane against polymerization used in a chemical vapor deposition process for silicon oxides in electronic material fabrication and stabilized for extended periods of heating, comprising; providing an effective amount of a free radical polymerization inhibitor to said cyclotetrasiloxane having the following formula:

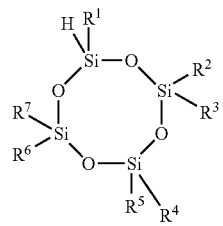

where $R^{1-7}$ are individually selected from the group consisting of hydrogen, a normal, branched or cyclic $C_{1-10}$ alkyl group, and a $C_{1-4}$ alkoxy group, wherein said free radical scavenger is selected from the group consisting of: 2,6-ditert-butyl-4-methyl phenol, 2,2,6,6-tetramethyl-1-piperidinyloxy, 2,6-dimethylphenol, 2-tert-butyl-4-hydroxyanisole, 3-tert-butyl-4-hydroxyanisole, propyl ester 3,4,5-trihydroxy-benzoic acid, 2-(1,1-dimethylethyl)-1,4 benzenediol, diphenylpicrylhydrazyl, 4-tert-butylcatechol, N-methylaniline, 2,6-dimethylaniline, p-methoxydiphenylamine, diphenylamine, N,N'-diphenyl-p-phenylenediamine, p-hydroxydiphenylamine, phenol, octadecyl-3-(3,5-di-tert-butyl-4 -hydroxyphenyl) propionate, tetrakis (methylene (3,5-di-tert-butyl-4-hydroxy-hydrocinnamate) methane, phenothiazines, alkylamidonoisoureas, thiodiethylene bis (3,5,-di-tert-butyl-4-hydroxy-hydrocinnamate, 1,2,-bis (3,5-di-tert-butyl-4-hydroxyhydrocinnamoyl) hydrazine, tris (2-methyl-4-hydroxy-5-tert-butylphenyl) butane, cyclic neopentanetetrayl bis (octadecyl phosphite), 4,4'-thiobis (6-tert-butyl-m-cresol, 2,2'-methylenebis (6-tert-butyl-p-cresol), oxalyl bis (benzylidenehydrazide) and mixtures thereof.

2. The process of claim 1 wherein said free radical scavenger is 2,6-di-tert-butyl-4-methyl phenol.

3. A process for stabilizing a cyclotetrasiloxane against polymerization used in a chemical vapor deposition process for silicon oxides in electronic material fabrication, comprising; providing an effective amount of a free radical polymerization inhibitor to said cyclotetrasiloxane having the following formula:

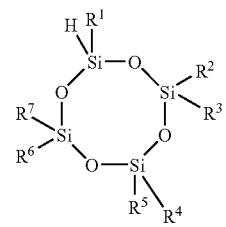

where $R^{1-7}$ are individually selected from the group consisting of hydrogen, a normal, branched or cyclic $C_{1-10}$ alkyl group, and a $C_{1-4}$ alkoxy groups wherein said free radical scavenger is provided in an amount of 10–1000 ppm (wt.).

4. The process of claim 3 wherein said free radical scavenger is provided in an amount of 50–500 ppm (wt.).

5. The process of claim 3 wherein said free radical scavenger is provided in an amount of 50–250 ppm (wt.).

6. The process of claim 3 wherein said free radical scavenger is provided in an amount of 100–200 ppm (wt.).

7. A process for stabilizing 1,3,5,7-tetramethylcyclotetrasiloxane against polymerization for extended periods of heating and caused by oxygen, carbon dioxide and/or nitrogen trifluoride used in a chemical vapor deposition process for silicon oxides in electronic material fabrication comprising providing a free radical scavenger to said 1,3,5,7-tetramethylcyclotetrasiloxane.

8. The process of claim 7 wherein said free radical scavenger is selected from the group consisting of 2,6-di-tert-butyl-4-methyl phenol, 2,2,6,6-tetramethyl-1-piperidinyloxy and mixtures thereof.

9. A composition of 1,3,5,7-tetramethylcyclotetrasiloxane stabilized against polymerization for extended periods of heating and used in a chemical vapor deposition process as a precursor for silicon oxides in electronic material fabrication comprising 1,3,5,7-tetramethylcyclotetrasiloxane and a free radical scavenger polymerization inhibitor.

10. A composition of 1,3,5,7-tetramethylcyclotetrasiloxane, used in a chemical vapor deposition process as a precursor for silicon oxides in electronic material fabrication, and stabilized against polymerization for extended periods of heating, comprising (a) 1,3,5,7-tetramethylcyclotetrasiloxane, (b) a free radical scavenger selected from the group consisting of 2,6-di-tert-butyl-4-methyl phenol, 2,2,6,6-tetramethyl-1-piperidinyloxy, 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl) propionate, tetrakis (methylene (3,5-di-tert-butyl)-4-hydroxy-hydrocinnamate) methane, phenothiazines, alkylamidonoisoureas, thiodiethylene bis (3,5,-di-tert-butyl-4-hydroxy-hydrocinnamate, 1,2,-bis (3,5-di-tert-butyl-4-hydroxyhydrocinnamoyl) hydrazine, tris (2-methyl-4-hydroxy-5-tert-butylphenyl) butane, cyclic neopentanetetrayl bis (octadecyl phosphite), 4,4'-thiobis (6-tert-butyl-m-cresol), 2,2'-methylenebis (6-tert-butyl-p-cresol), oxalyl bis (benzylidenehydrazide) and mixtures thereof.

* * * * *